United States Patent
Campbell et al.

(10) Patent No.: US 10,678,213 B2
(45) Date of Patent: Jun. 9, 2020

(54) INTRINSICALLY-SAFE HANDHELD FIELD MAINTENANCE TOOL WITH IMPROVED HELP FUNCTION

(71) Applicant: Fisher-Rosemount Systems, Inc., Round Rock, TX (US)

(72) Inventors: Susan A. Campbell, Shakopee, MN (US); Christopher G Kasic, Minneapolis, MN (US); Christopher P Kantzes, Minneapolis, MN (US)

(73) Assignee: Fisher-Rosemount Systems, Inc., Round Rock, TX (US)

( * ) Notice: Subject to any disclaimer, the term of this patent is extended or adjusted under 35 U.S.C. 154(b) by 32 days.

(21) Appl. No.: 15/423,860

(22) Filed: Feb. 3, 2017

(65) Prior Publication Data

US 2017/0146977 A1 May 25, 2017

Related U.S. Application Data

(63) Continuation-in-part of application No. 13/191,644, filed on Jul. 27, 2011, now Pat. No. 9,709,973.
(Continued)

(51) Int. Cl.
*G05B 19/409* (2006.01)
*G06Q 20/20* (2012.01)
(Continued)

(52) U.S. Cl.
CPC ........ *G05B 19/409* (2013.01); *C07C 29/1518* (2013.01); *G05B 19/042* (2013.01);
(Continued)

(58) Field of Classification Search
USPC .......................................................... 340/6.1
See application file for complete search history.

(56) References Cited

U.S. PATENT DOCUMENTS 6,199,061 B1 * 3/2001 Blewett .............. G06F 16/3334
6,266,726 B1 * 7/2001 Nixon ................ G05B 19/0421
710/105
(Continued)

FOREIGN PATENT DOCUMENTS

GB        2552421 A       1/2018
JP      202244729 A       8/2002
(Continued)

OTHER PUBLICATIONS

"Zetakey Webkit Browser" retrieved from https://www.zetakey.com/browser.php, Zetkey Solutions Limited 2016, 5 pages.
(Continued)

*Primary Examiner* — Emily C Terrell
(74) *Attorney, Agent, or Firm* — Christopher R. Christenson; Kelly, Holt & Christenson PLLC

(57) ABSTRACT

An intrinsically-safe handheld field maintenance tool includes a controller, a process communication module, and a display. The process communication module is configured to communicate with a field device using a process communication protocol. The display is coupled to the controller. A user interface module is also coupled to the controller and is configured to receive user input. The controller is configured to detect a user input help request and provide a video output on the display in response to the user input help request.

19 Claims, 5 Drawing Sheets

Related U.S. Application Data

(60) Provisional application No. 61/368,477, filed on Jul. 28, 2010.

(51) Int. Cl.
- *G06Q 40/04* (2012.01)
- *C07C 29/151* (2006.01)
- *G06Q 10/06* (2012.01)
- *G06Q 30/06* (2012.01)
- *G05B 19/042* (2006.01)
- *G05B 19/4068* (2006.01)

(52) U.S. Cl.
CPC ..... *G05B 19/0426* (2013.01); *G05B 19/4068* (2013.01); *G06Q 10/06315* (2013.01); *G06Q 20/204* (2013.01); *G06Q 30/0601* (2013.01); *G06Q 40/04* (2013.01); *G05B 2219/23018* (2013.01); *G05B 2219/23054* (2013.01); *G05B 2219/23126* (2013.01); *G05B 2219/23163* (2013.01); *G05B 2219/23406* (2013.01); *G05B 2219/23445* (2013.01); *G05B 2219/23446* (2013.01); *G05B 2219/24001* (2013.01); *G05B 2219/24056* (2013.01); *G05B 2219/25062* (2013.01); *G05B 2219/25428* (2013.01); *G05B 2219/31121* (2013.01); *G05B 2219/31197* (2013.01); *G05B 2219/31475* (2013.01); *G05B 2219/32007* (2013.01); *G05B 2219/32144* (2013.01); *G05B 2219/32226* (2013.01); *G05B 2219/33331* (2013.01); *G05B 2219/35422* (2013.01); *G05B 2219/35429* (2013.01); *G05B 2219/36122* (2013.01); *G05B 2219/36128* (2013.01); *G05B 2219/50193* (2013.01); *Y02P 90/14* (2015.11); *Y04S 10/54* (2013.01)

(56) References Cited

U.S. PATENT DOCUMENTS

| | | | |
|---|---|---|---|
| 6,574,672 B1 * | 6/2003 | Mitchell | G06F 1/163 709/200 |
| 6,671,854 B1 * | 12/2003 | Dunsmoir | G06F 17/2247 707/999.101 |
| 8,001,470 B1 | 8/2011 | Chen et al. | |
| 9,411,759 B2 | 8/2016 | Ramsay | |
| 2003/0058267 A1 | 3/2003 | Warren | |
| 2003/0093539 A1 * | 5/2003 | Simeloff | G06F 21/31 709/229 |
| 2003/0160828 A1 * | 8/2003 | Treibach-Heck | G06F 3/0482 715/780 |
| 2004/0230821 A1 * | 11/2004 | Mathiowetz | G06F 21/31 713/193 |
| 2005/0154985 A1 | 7/2005 | Burkhart | |
| 2007/0078526 A1 * | 4/2007 | Bromley | G05B 19/0423 700/19 |
| 2007/0277104 A1 * | 11/2007 | Hennum | G06F 9/453 715/705 |
| 2008/0072139 A1 | 3/2008 | Salinas et al. | |
| 2010/0011067 A1 * | 1/2010 | Allstrom | H04L 51/04 709/206 |
| 2011/0191058 A1 * | 8/2011 | Nielsen | B65D 83/203 702/130 |
| 2012/0038458 A1 | 2/2012 | Toepke et al. | |
| 2012/0147179 A1 * | 6/2012 | Kim | G07C 9/00087 348/143 |
| 2013/0174017 A1 | 7/2013 | Richardson et al. | |
| 2014/0245142 A1 | 8/2014 | Dresti et al. | |
| 2018/0024847 A1 | 1/2018 | Campbell et al. | |

FOREIGN PATENT DOCUMENTS

| | | |
|---|---|---|
| JP | 2007072825 A | 3/2007 |
| JP | 2008520050 A | 6/2008 |
| WO | 2012016004 A2 | 2/2012 |

OTHER PUBLICATIONS

"HTML5 Introduction—What is New in HTML5", retrieved at https://w3schools.com/html/html5_intro.asp, retrieved on Jul. 21; 2017, 4 pages.

Combined Search and Examination Report dated May 25, 2018 for United Kingdom Patent Application No. 1720241.7, 10 pages.

Office Action dated Jan. 15, 2019 for Japanese Patent Application No. 2017-226547, 7 pages including English translation.

Prosecution Hisory for U.S. Appl. No. 15/216,943 including: Examiner's Answer to Appeal Brief dated Sep. 11, 2019, Advisoy Action dated Jan. 29, 2019, Final Office Action dated Oct. 17, 2018, Non-Final Office Action dated Apr. 9, 2018, 100 pages.

Search Report for Application No. GB1710265.8, dated Oct. 25, 2017, 3 pages.

* cited by examiner

INTRINSICALLY-SAFE HANDHELD FIELD MAINTENANCE TOOL WITH IMPROVED HELP FUNCTION

CROSS-REFERENCE TO RELATED APPLICATION

The present application is a Continuation-In-Part application of U.S. patent application Ser. No. 13/191,644, filed Jul. 27, 2011, which is based on and claims the benefit of U.S. Provisional Patent Application Ser. No. 61/368,477, filed Jul. 28, 2010.

BACKGROUND

Handheld field maintenance tools are known. Such tools are highly useful in the process control and measurement industry to allow operators to conveniently communicate with and/or interrogate field devices in a given process installation. Examples of such process installations include petroleum, pharmaceutical, chemical, pulp, and other fluid processing installations. In such installations, the process control and measurement network may include tens or even hundreds of various field devices which periodically require maintenance to ensure that such devices are functioning properly and/or calibrated. Moreover, when one or more errors in the process control and measurement installation are detected, the use of a handheld field maintenance tool allows a technician to quickly diagnose such errors in the field. Handheld field maintenance tools are generally used to configure, calibrate, and diagnose problems relative to intelligent field devices using digital process communication protocols.

Since at least some process installations may involve highly volatile, or even explosive, environments, it is often beneficial, or even required, for field devices and the handheld field maintenance tools used with such field devices to comply with intrinsic safety requirements. These requirements help ensure that compliant electrical devices will not generate a source of ignition even under fault conditions. One example of Intrinsic Safety requirements is set forth in: APPROVAL STANDARD INTRINSICALLY SAFE APPARATUS AND ASSOCIATED APPARATUS FOR USE IN CLASS I, II and III, DIVISION NUMBER 1 HAZARDOUS (CLASSIFIED) LOCATIONS, CLASS NUMBER 3610, promulgated by Factory Mutual Research October, 1998.

In the past, intrinsically-safe handheld field maintenance tools had relatively few options for displaying help content. Much of the help content was limited to describing a single option on a screen. If a user or technician required additional information, he or she typically had to consult a printed or on-line manual which may or may not have been accessible when needed. Given that the process environment may have hundreds or thousands of different field devices and that the varied operations for which handheld field maintenance tools are used is becoming increasingly complex, it is even more important to provide a user with an efficient, rich and comprehensive help system in such a device.

SUMMARY

An intrinsically-safe handheld field maintenance tool includes a controller, a process communication module, and a display. The process communication module is configured to communicate with a field device using a process communication protocol. The display is coupled to the controller. A user interface module is also coupled to the controller and is configured to receive user input. The controller is configured to detect a user input help request and provide a video output on the display in response to the user input help request.

DETAILED DESCRIPTION

Figure 1A:
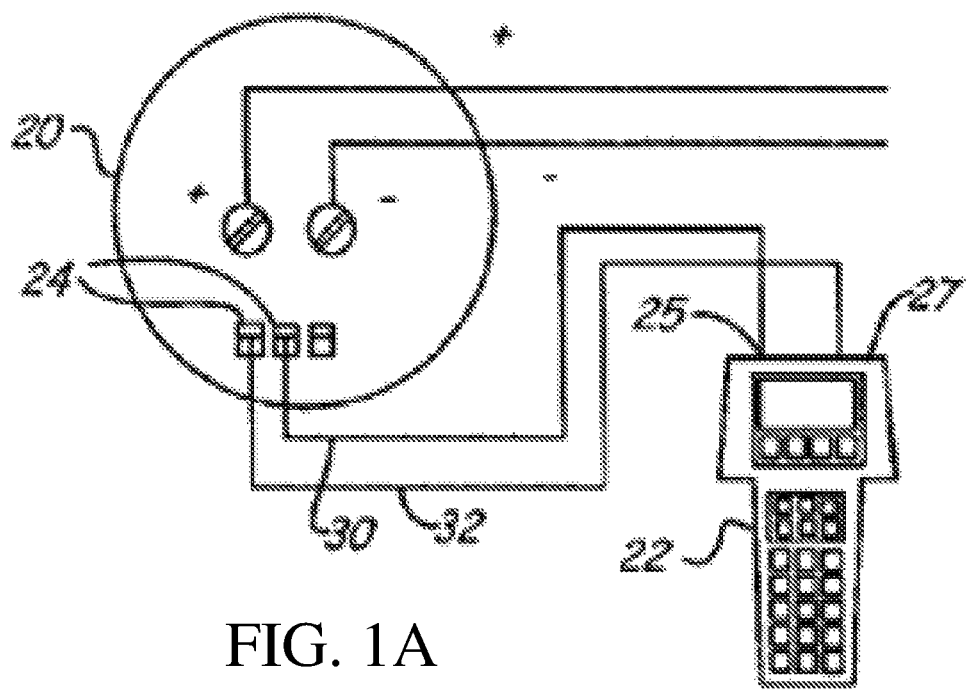
FIGS. 1A and 1B are diagrammatic views of a handheld field maintenance tool with which embodiments of the invention are particularly useful.
Figure 1B:
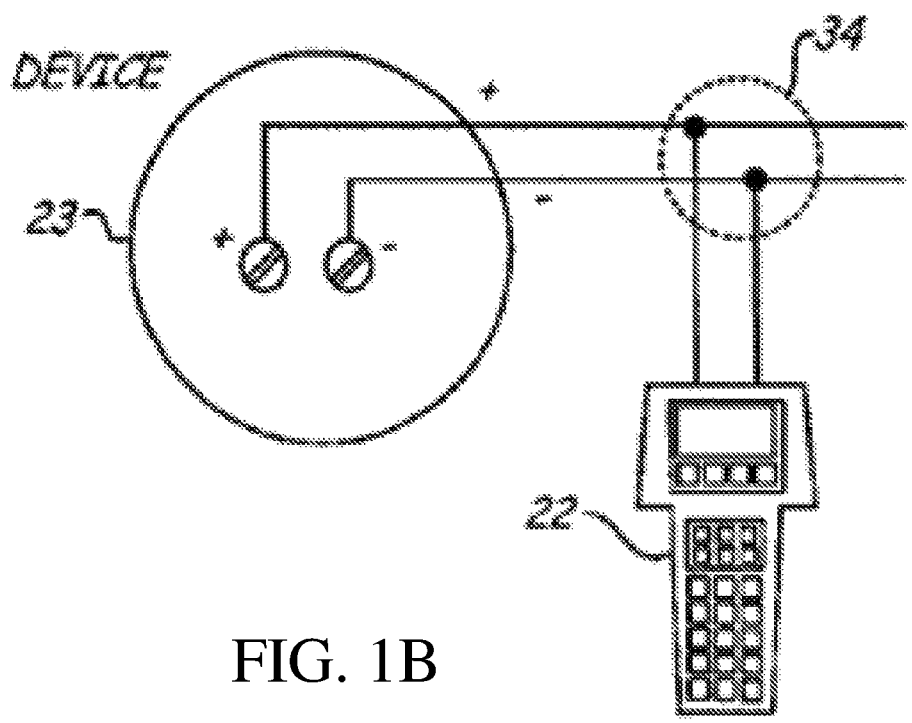

FIGS. 1A and 1B are diagrammatic views of a handheld field maintenance tool 22 coupled to field devices 20, 23. As shown in FIG. 1A, handheld field maintenance tool 22 includes a pair of terminals 25, 27 that couple to test leads 30, 32, respectively, which are then coupled to terminals 24 of field device 20. Terminals 24 may be dedicated terminals to allow such a handheld field maintenance tool to couple to device 20 and interact with device 20. The utilization of terminals 25, 27 to couple to field device illustrates an example of a wired connection between handheld field maintenance tool 22 and field device 20.

FIG. 1B shows an alternate arrangement where handheld field maintenance tool 22 couples directly to the process control loop 34 to which field device 23 is coupled. In either case, the wired connection between the handheld field maintenance tool and the field device allows the handheld field maintenance tool to interact with the desired field device 20, 23.

Figure 2:
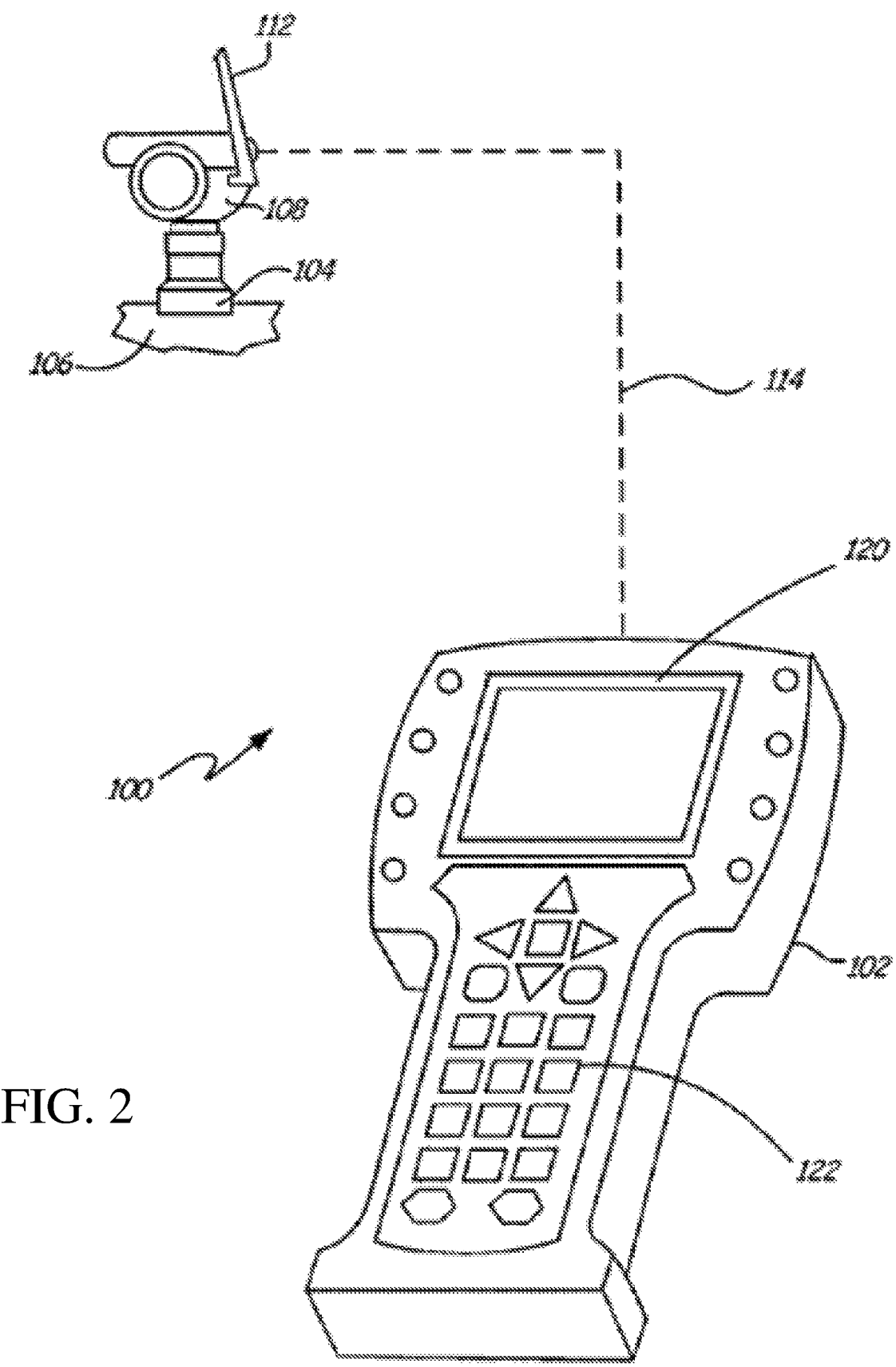
FIG. 2 is a diagrammatic view of a handheld field maintenance tool with which embodiments of the present invention are particularly useful.

FIG. 2 is a diagrammatic view of handheld field maintenance tool 102 interacting with wireless field device 104. System 100 includes handheld field maintenance tool 102 communicating with field device 104. Handheld field maintenance tool 102 is communicatively coupled to field device 104 via communication link 114. Communication link 114 can take any suitable form including wired connections as shown in FIGS. 1A and 1B, as well as wireless communication techniques that are currently being used or being developed. Handheld field maintenance tool 102 allows a technician to interact with field device 104 to configure, calibrate, and/or diagnose problems with respect to field device 104 using a digital process communication protocol such as FOUNDATION™ Fieldbus and/or the HART® protocol. Handheld field maintenance tools, such as tool 102 can be used to save configuration data from field devices, such as field device 104.

Field device 104 may be any device that senses a variable in the process and transmits information related to the variable over a process communication loop; such as a pressure or temperature. Field device 104 may also be a device that receives information from a process communication loop and sets a physical parameter, such as a valve closure, based on the information. Field device 104 is depicted as an industrial process fluid pressure transmitter having a pressure manifold 106 coupled thereto, and an electronics enclosure 108. Field device 104 is provided for illustrative purposes only. In reality, field device 104 may be any industrial device, such as a process fluid temperature transmitter, process fluid level transmitter, process fluid flow transmitter, valve controller, or any other device that is useful in the measurement and/or control of industrial processes.

Handheld field maintenance tool 102 generally includes a user interface that comprises a display 120 as well as a number of input buttons 122. Display 120 may be any suitable display such as an active-matrix liquid crystal display, or any other suitable display, including a touch screen, that is able to provide useful information. Buttons 122 in addition to or instead of a touch screen may comprise any suitable arrangement relative any number of functions to which the handheld field maintenance tool may be directed. Buttons 122 may comprise a numeric keypad, an alphanumeric keypad, any suitable number of custom functions and/or navigation buttons, or any suitable combination thereof. Further still, additional buttons may be provided via an on-screen keyboard or display that the user can use in addition to or in place of physical buttons.

Figure 3:
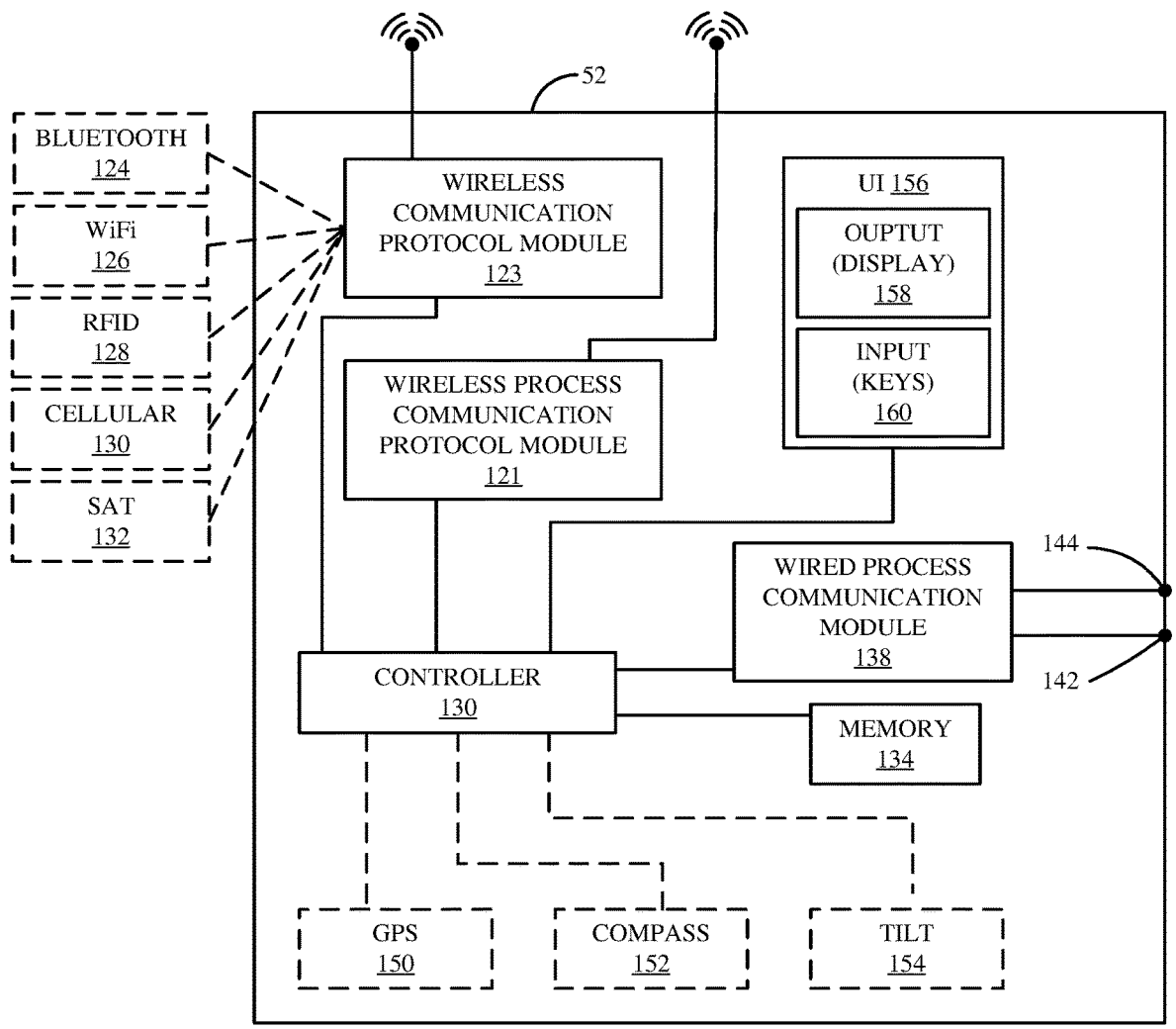
FIG. 3 is a block diagram of a handheld field maintenance tool in accordance with an embodiment of the present invention.

FIG. 3 is a diagrammatic system block diagram of a handheld field maintenance tool in accordance with the embodiment of the present invention. It is preferred that tool 52 employ circuitry that complies with at least one intrinsic safety specification, such as that listed above, to help ensure safety in potentially explosive environments. Handheld field maintenance tool 52 preferably includes at least one wireless process communication module 121. Suitable examples for wireless process communication module 121 include a module that generates and/or receives proper signals in accordance with a known wireless process communication protocol, such as the known WirelessHART protocol (IEC 62591). Another wireless process communication protocol is set forth in ISA100.11a. While FIG. 3 shows a single wireless process communication module 121, it is expressly contemplated that any suitable number of wireless process communication modules can be used to communicate in accordance with various wireless process communication protocols now in existence or later developed.

Handheld field maintenance tool 52 also includes at least one secondary wireless communication protocol module 123. Wireless communication protocol module 123 can communicate in accordance with one or more of the options shown in phantom in FIG. 3. Specifically, wireless communication protocol module 123 may communicate in accordance with a Bluetooth specification 124 (such as Bluetooth Specification 2.1 rated at Power Class 2); a Wi-Fi specification 126 (such as IEEE 802.11.a/b/g/n); a known RFID specification 128; cellular communication techniques 130 (such as GSM/CDMA); WiMAX (IEEE 802.16m), and/or satellite communication 132. These communication techniques and methodologies allow handheld field maintenance tool 52 to communicate directly with a wireless gateway or other suitable device either via direct wireless communication, or using the Internet. While one wireless communication protocol module 123 is shown in FIG. 3, any suitable number may be used. Each of the wireless process communication protocol module 121 and wireless communication protocol module 123 is coupled to controller 130 which is also coupled to the wired process communication module 138.

Controller 130 is preferably a microprocessor that executes a sequence of instructions stored therein, or in memory 134 coupled to controller 130, to perform handheld field maintenance tasks. Wired process communication module 138 allows handheld field maintenance tool 52 to be physically coupled via a wired connection using one or more different physical terminals disposed on the handheld field maintenance tools (terminals 142, 144 are shown for example). Terminals 142, 144 in addition to various other terminals that may be present on the handheld field maintenance tool facilitate a wired connection to a field device. Examples of suitable wired process communication can include the Highway Addressable Remote Transducer (HART®) protocol, the FOUNDATION™ Fieldbus protocol, Profibus and others.

Handheld field maintenance tool 52 includes a user interface module 156 for generating a user interface using display 120 and keys 122. Module 156 can include suitable display driver circuitry 158 and/or memory to interact with display 120. Module 156 also includes input circuitry 160 which is configured to interact with buttons 122 to receive user input. Additionally, in embodiments where display 120 includes a touchscreen, module 160 can include circuitry to generate user input data to controller 130 based upon a user's touch and/or gestures received by the touchscreen.

Handheld field maintenance tool 52 can include a number of additional items that facilitate additional functionality. Specifically, tool 52 can include a position detection module, such as GPS module 150. GPS module 150 can be configured to additionally use the Wide Area Augmentation System (WAAS) for improved accuracy and/or can be configured to operate using differential GPS techniques as appropriate. Module 150 is coupled to controller 130 to provide controller 130 with an indication of the geographic position of tool 52. While position detection module 150 is preferably an internal component of tool 52, it may be external and communicatively coupled thereto using a suitable wireless or wired communication protocol, such as Bluetooth 124, RFID 128, et cetera. Further, while position detection module 150 is generally described as GPS module 150, other techniques for triangulating the position of the handheld field maintenance tool based upon relative strength of wireless communication with wireless transceivers having known fixed positions can be employed. Examples of such wireless triangulation techniques include triangulation of the position of handheld field maintenance tool 52 based upon communication with three or more fixed-position WiFi communication points, or access points. Further still, as set forth above, embodiments of the present invention may include the ability to employ one or more wireless process communication protocol modules, such as module 121. Such triangulation techniques can also be employed if a suitable number of wireless interactions with fixed-position wireless field devices can be achieved. Finally, while the various methods provided for obtaining the position of handheld field maintenance tool 52 are described above, they can also be used in conjunction with one another to provide additional accuracy and/or redundancy. Additionally, tool 52 also preferably comprises compass module 152 coupled to controller 130 such that tool 52 can indicate the compass direction in which it is pointing. Finally, tool 52 can also include tilt module 154 coupled to controller 130 to provide an indication to controller 130 relative to an angle of inclination of tool 52 relative to gravity. However, additional axes of sensing are also contemplated.

When one or more field devices are not functioning properly, the entire process installation may be affected. It is thus very important for problems with such devices to be identified and remedied as quickly as possible. Moreover, with modern smart field devices growing more complex, finding a root cause of a specific problem is becoming more difficult.

In accordance with embodiments of the present invention, a markup-based help system is provided that allows users to access help information or content about the handheld field maintenance tool's hardware and applications running thereon without needing to carry a printed manual or without access to a computer. The information is available on the handheld field maintenance tool itself and is accessible at any time. By using a responsive design, the markup-based content including images, diagrams, and potentially videos, can be pre-processed and automatically provided appropriately on the display screen of the handheld field maintenance tool. For example, the pre-processing may include re-sizing the help content for the size of the screen, and/or determining the physical orientation of the handheld field maintenance tool (portrait or landscape) and adjusting the help content appropriately. Additionally, since the help content is provided in the form of markup-based help, it may be pre-processed and appropriately rendered on a variety of different devices including a desktop computer, a tablet, smartphone, etc. Those different devices can access the markup-based help content and display or otherwise provide such content appropriately for their own screen size/orientations.

The provision of help content can be significantly guided by the automatic determination of context information by the handheld field maintenance tool. With such information, the handheld field maintenance tool can make relevant help information readily accessible to the technician should it be needed. Additionally, the context information may help locate more relevant help information quicker than would be the case if the technician merely selected a help button. Examples of such context information that can inform the handheld field maintenance tool about what the technician is currently doing includes, but is not limited to, digital interactions with a connected field device; errors or other diagnostic information provided by the field device; field device status information; field device audit trail information (preferably obtained wirelessly from an asset management system in real-time); asset history information (either stored locally in the handheld field maintenance tool or obtained wirelessly from a remote host); process parameters relative to the process installation, which are provided by one or more other field devices or the process controller; field device alert information (available from the connected field device or another field device); process alarm conditions; local environmental conditions (such as ambient temperature, barometric pressure, humidity, et cetera); measurement of electromagnetic interference using any of the wireless communication modules within the handheld field maintenance tool; vibration measurement; time of day; information relative to the technician (such as technician name or ID, technician security clearance, et cetera). Any such parameters, either alone or in combination with other parameters, can inform the handheld field maintenance tool about what the technician is currently doing. While the result of analyzing such information preferably helps identify: help information regarding a field device; help information regarding a field maintenance operation; and/or help information regarding a handheld field maintenance tool software application, it is expressly contemplated that a number of viable results can be determined with a statistical weight ranking the results. While such diverse information is preferably automatically analyzed by the handheld field maintenance tool in order to provide the most relevant help information to the technician, it is also contemplated that all such information can also be made available to the technician.

Figure 4:
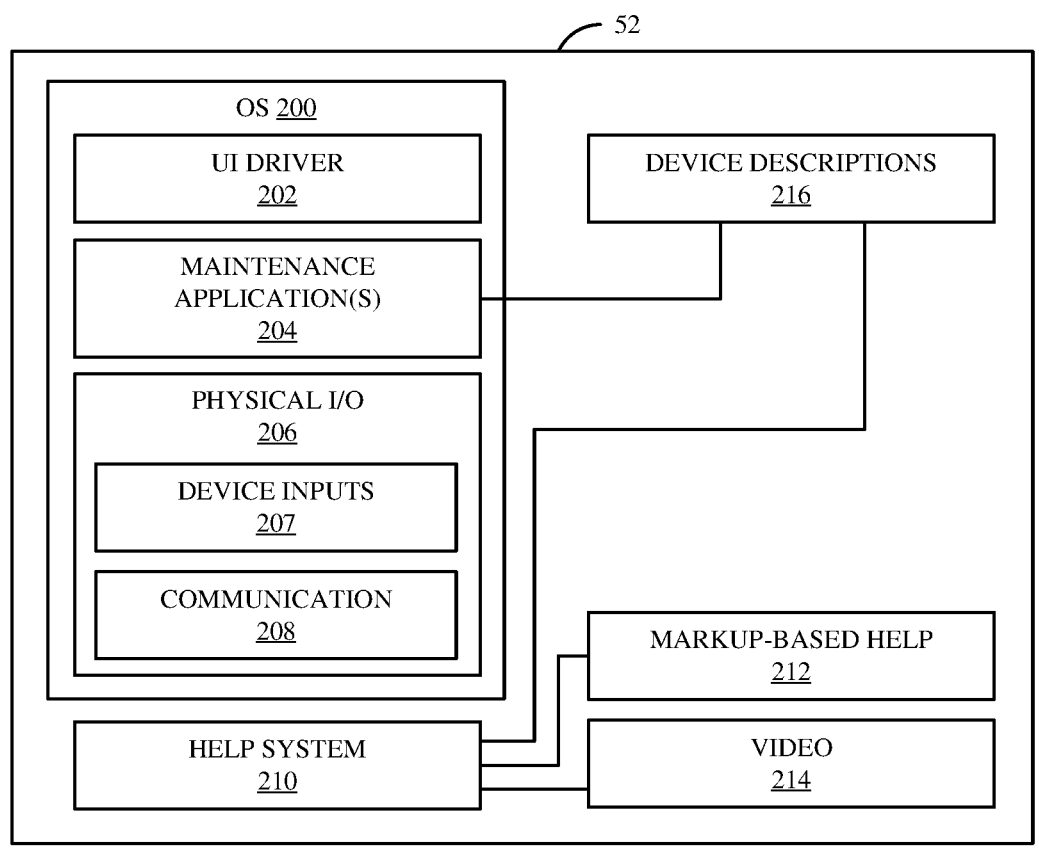
FIG. 4 is a logical block diagram of a handheld field maintenance tool in accordance with an embodiment of the present invention.

FIG. 4 is a logical block diagram of handheld field maintenance tool 52 in accordance with an embodiment of the present invention. The logical functionality of handheld field maintenance tool 52 is provided by controller 130 interacting with memory therein and/or memory 134 (shown in FIG. 3). FIG. 4 indicates that handheld field maintenance tool 52 generally includes an operating system 200, which may be any suitable operating system for an intrinsically-safe handheld field maintenance tool. In one example, operating system 200 is that sold under the trade designation Windows Embedded Compact 2013, available from Microsoft Corporation of Redmond, Wash. However, other suitable examples include embedded Linux, Android, FreeBSD, FreeRTOS, ThreadX, QNX, etc. In the example shown in FIG. 4, operating system 200 includes a user interface driver component 202 that is adapted to interact with display 120, which may be a touch screen display, and/or buttons 122. Accordingly, UI driver component 202 may provide suitable signals to generate graphical representations on display 120 and sense or otherwise obtain user input as a user touches screen 120. Similarly, UI driver component 202 may also be configured to interact with or otherwise sense individual presses of buttons 122 in order to allow the user to interact with the handheld field maintenance tool. Operating system 200 may also include or be configured to support one or more maintenance applications 204. These maintenance applications 204 may be installed or otherwise provided on the handheld field maintenance tool to perform specific maintenance functions, such as troubleshooting a field device, documenting a field device's operation, troubleshooting a process communication loop, calibrating a field device, et cetera. Accordingly, the number of maintenance applications 204 present on the handheld field maintenance device 52 may vary depending on the various functions for which the handheld field maintenance tool is used. Additionally, operating system 200 generally includes or otherwise is coupled to physical input/output module 206. Such physical input/output, in the example shown, includes generating and/or measuring signals present through one or more terminals of the handheld field maintenance tool, such as terminals 142, 144 (shown in FIG. 3), as indicated at block 207. Additionally, physical input/output module 206 can also include a communication component 208 that supports a communication stack, such as TCP/IP to allow handheld field maintenance tool 52 to communicate with external devices using either wireless process communication protocol module 123 or wireless process communication protocol module 121. By virtue of such communication, handheld field maintenance tool 52 may obtain additional or supplemental help content in the event that the help content stored on handheld field maintenance tool 52 is insufficient.

In accordance with an embodiment of the present invention, intrinsically-safe handheld field maintenance tool 52 includes help system 210 that is configured to provide advanced help functionality to the user of the handheld field maintenance tool. Help system 210 includes or is otherwise coupled to markup-based help content 212, video help store 214 and device description store 216. Markup-based help content 212 is assistive content that includes at least one markup tag or indicator that describes the assistive content. In one example, markup-based help content 212 is authored in accordance with the hypertext markup language (HTML).

This is a standardized system for tagging text files or other content in order to achieve font, color, graphic, and hyperlink effects on World Wide Web pages. A more recent evolution of the HTML standard is HTML5. Additional elements present in HTML5 include multi-media elements such as audio and video. Accordingly, in at least one embodiment, video help store 214 may be stored with markup-based help content 212 and the video content may be indicated by the markup tags. Additionally, device descriptions store 216 may also provide field device-specific help or other content that may be useful to the user. At the very least, individual device description content 216 may include a URL or other suitable indicator that allows the handheld field maintenance tool to obtain supplemental help content while the user is in the field from a remote device (such as a server operated by the field device manufacturer) that is able to provide additional markup-based help content to the handheld field maintenance tool 52 which may then be suitably sized and oriented for display on display 120.

Figure 5:
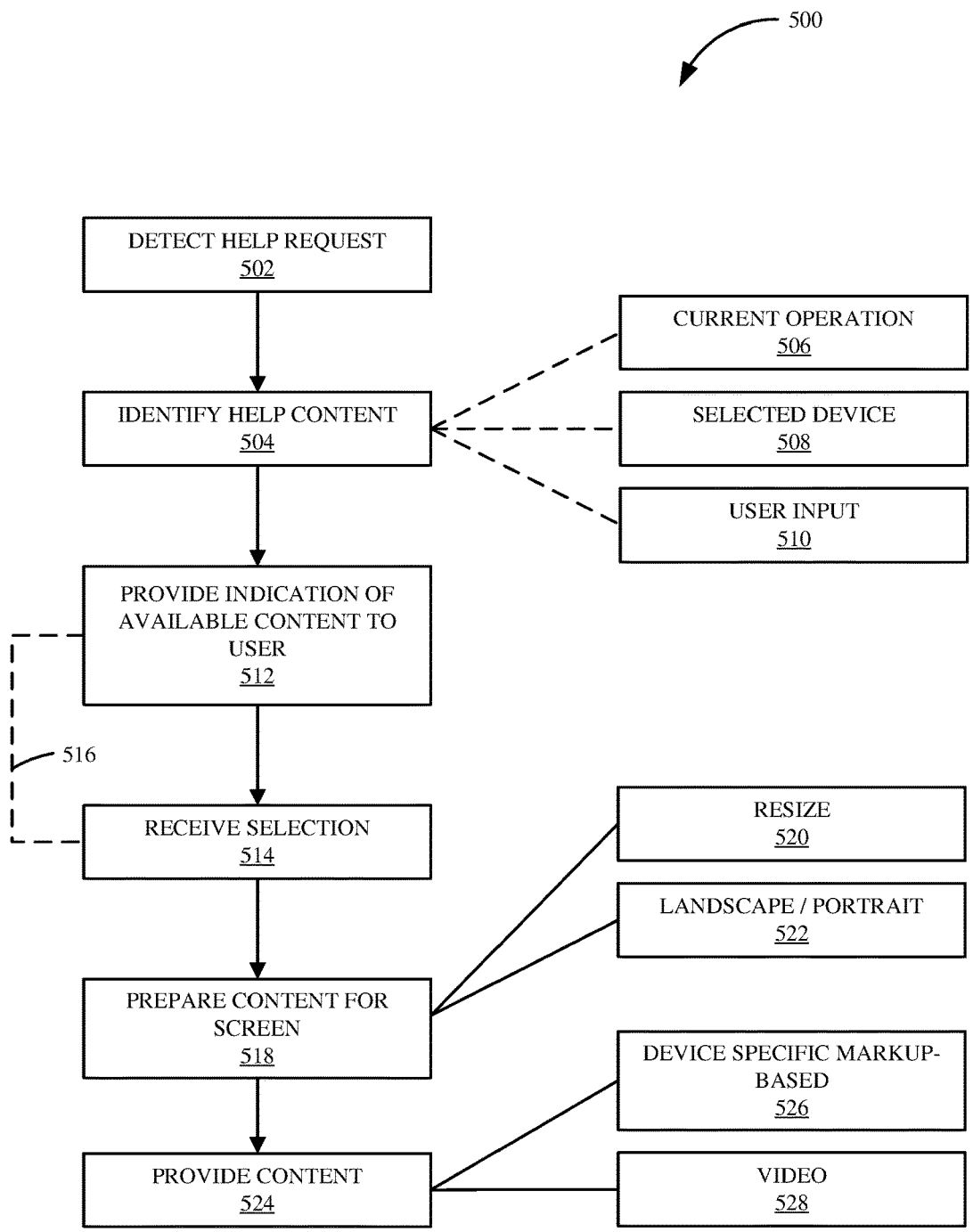
FIG. 5 is a flow diagram of a method of providing help to a user of a handheld field maintenance tool in accordance with an embodiment of the present invention.

FIG. 5 is a flow diagram of a method of providing help to a user of a handheld field maintenance tool in accordance an embodiment of the present invention. Method 500 begins at block 502 where a user of the handheld field maintenance tool generates a help request that is detected by the handheld field maintenance tool. This may be done by the user pressing a specific help button 122 or a button displayed on display 120, in the event that display 120 is a touch screen. Upon detecting the help request, method 500 passes to block 504 where help content relative to the help request is identified. Such identification of available help content can be informed by context information such as a current field device operation being performed by the user using the handheld field maintenance tool, as indicated at block 506; an indication of a selected field device such as a device to which the handheld field maintenance tool is currently coupled or a field device that is selected by the user, as indicated at block 508; and/or specific user input as indicated at block 510. An example of such specific user input is the user simply navigating to a particular field maintenance operation or field device or any combination thereof and then selecting the help function. At block 512, an indication of the available content is provided to the user. This indication may be one or more topics that match the operation, field device, or user input identified at block 504 that are stored within markup-based help content 212 and/or video help store 214. At block 514, a user input is received. The user input at block 514 may be a selection of one or more of the displayed markup-based help content topics available on the handheld field maintenance tool indicated at block 512. Additionally, or alternatively, the user input may be an indication that none of the displayed content is useful to the user. In that case, the handheld field maintenance tool may use a wireless communication link, if available, to obtain additional or supplemental help content regarding the help request. In such case, method 500 may return to block 512 to provide such additional help content, as indicated by phantom line 516. Once the user has selected at least some help content for display, control passes to block 518 where the content is prepared for on-screen display. As described above, since the help content in accordance with embodiments of the present invention is generally provided in the form of markup-based help content, it may be easily re-sized for the precise size of display screen 120. This is indicated at block 520. Additionally, the current orientation of the handheld field maintenance tool can be determined (in any suitable manner) and the content can be oriented based on the current handheld field maintenance tool orientation, as indicated at block 522. Next, at block 524, the re-sized and properly oriented help content is provided to the user via display 120 and potentially through an audio output channel, such as using speakers or a wireless Bluetooth connection to an earpiece of the user. The content can take a variety of forms and is preferably device-specific markup-based content, as indicated at block 526. This can be graphical content showing diagrams of the handheld field maintenance tool and appropriate connections to a field device for a particular function. The content may include one or more video presentations showing the user how to perform a particular function or how to make a particular connection to a field device, as indicated at block 528. As can be appreciated, using the rich markup-based help content of embodiments of the present invention, the user can receive a wide variety of different types of help content that is particularly suited to the field device and/or function with which the user is interacting.

While embodiments of the present invention generally described the help content as either being provided or otherwise stored within the handheld field maintenance tool or potentially available via a wireless connection, it is also contemplated that the help content could be dynamically updated when the handheld field maintenance tool achieves a particular connection to the Internet. For example, if a user generates a help request and ultimately no help is available, that particular help request may be logged or otherwise queued in help system 210 such that when the handheld field maintenance tool is located within a wireless hotspot where a Wi-Fi connection is available, additional help content can be downloaded or otherwise obtained from a remote device, such as a server of the field device manufacturer, so that when the user returns to the field device, the help content is subsequently available.

While embodiments of the present invention generally obtain and process significant amounts of diagnostic and/or contextual information, it is preferred that at least some embodiments of the present invention provide the technician with device-specific help information as desired. For example, the technician may select the "help" function or key, and the handheld field maintenance tool automatically generates a query to a remote host or system relative to the specific field device to which the handheld field maintenance tool is communicatively coupled. The query results are received wirelessly and displayed to the technician. Preferably, the help results are analyzed based on current field device context information, and more particular items of help information are offered to the technician based on the context information. Help results can include any information that is helpful to the technician drawn from any source, local or remote. Examples of help results include help information from a field device manual, a list of tasks (with links to the DD tasks) to perform based on the status, as well as one or more resources to "fix" the field device. Help results can also include links to videos where the technician is shown how to diagnose/troubleshoot/fix the field device. In embodiments where the handheld field maintenance tool has sufficient memory capacity, all device-specific help information may actually be stored locally. However, in such embodiments, it is still preferred that the help query results be ordered or organized based on the context information. Thus, if a technician is performing a specific calibration operation on a specific field device and presses the help button, the result will be device-specific help information, and the highest ranking result will be directed to the calibration operation the technician is currently performing.

Although the present invention has been described with reference to particular embodiments, workers skilled in the art will recognize that changes may be made in form and detail without departing from the spirit and scope of the invention.

What is claimed is:

1. An intrinsically-safe handheld field maintenance tool comprising:
    a controller configured to automatically obtain context information prior to detecting a user input help request;
    a process communication module communicating with a field device using a process communication protocol;
    a display coupled to the controller;
    a user interface module coupled to the controller and receiving user input; and
    wherein, upon detecting the user input help request, the controller is configured to use the context information to responsively accesses help video content that is tagged as video content in a markup language to obtain help video content results and to apply a statistical weight to rank the help video content results to identify selected video content, and pre-processes the selected video content to render a video output on the display, the video output being in response to the user input help request.

2. The intrinsically-safe handheld field maintenance tool of claim 1, wherein the controller provides a listing of help information in response to the user input help request and provides the video output in response to user input selecting an item from the listing of help information.

3. The intrinsically-safe handheld field maintenance tool of claim 2, wherein the context information is further based on digital interactions with a connected field device.

4. The intrinsically-safe handheld field maintenance tool of claim 3, wherein the context information includes diagnostic information provided by the field device to the handheld field maintenance tool.

5. The intrinsically-safe handheld field maintenance tool of claim 1, wherein the controller is, configured to receive the user input help request via a touchscreen on the display.

6. The intrinsically-safe handheld field maintenance tool of claim 1, wherein the video output is generated by a link that causes the handheld field maintenance tool to communicatively couple to a remote server and download a video presentation.

7. The intrinsically-safe handheld field maintenance tool of claim 6, wherein the video presentation is directed to a field device to which the intrinsically-safe handheld field maintenance tool, is coupled.

8. The intrinsically-safe handheld field maintenance tool of claim 7, wherein the video presentation is directed to diagnosing the field device.

9. The intrinsically-safe handheld field maintenance tool of claim 7, wherein the video presentation is directed to fixing the field device.

10. The intrinsically-safe handheld field maintenance tool of claim 1, and further comprising a wireless communication protocol module configured to communicatively couple to a remote server and execute a query in response to the user input help request wherein the query is based on a field device to which the intrinsically-safe handheld field maintenance tool is coupled.

11. The intrinsically-safe handheld field maintenance tool of claim 10, wherein the wireless communication module is configured to receive query results from the remote server and wherein the controller is configured to rank the query results based on context information of the intrinsically-safe handheld field maintenance tool.

12. An intrinsically-safe handheld field maintenance tool comprising:
    a controller configured to automatically obtain context information prior to detecting a user input help request;
    a process communication module communicating with a field device using a process communication protocol;
    a display coupled to the controller;
    a user interface module coupled to the controller and receiving user input; and
    wherein the controller, upon detecting the user input help request, is configured to use the context information to engage a help system to access a markup based help content store to obtain markup-based help content including video help content tagged as video content in a markup language to obtain video help content results and to apply a statistical weight to rank the video help results to identify selected video content and pre-process the selected video content to render the markup-based help content on the display.

13. The intrinsically-safe handheld field maintenance tool of claim 12, wherein the help system is configured to access a device description store to provide field device-specific help.

14. The intrinsically-safe handheld field maintenance tool of claim 12, wherein the markup-based help content is in accordance with the HyperText Markup Language.

15. The intrinsically-safe handheld field maintenance tool of claim 14, wherein the pre-processing includes resizing the video help content for the output on the display.

16. The intrinsically-safe handheld field maintenance tool of claim 14, wherein the pre-processing includes changing an orientation of the video help content for output on the display.

17. A method of providing help content on an intrinsically-safe handheld field maintenance tool, the method comprising:
    communicatively coupling the intrinsically-safe handheld field maintenance tool to a field device;
    obtaining context information automatically to make relevant help information accessible to a user;
    receiving a user input requesting help;
    using the context information to access video help content tagged as video content in a markup language to obtain video help content results and to apply statistical weight to rank the video help content results to identify selected video content; and
    pre-processing the selected video content to render the tagged video help content on a display of the intrinsically-safe handheld field maintenance tool.

18. The method of claim 1, wherein the video help content is related to the field device.

19. The intrinsically-safe handheld field maintenance tool of claim 1, wherein the help video content is stored in the intrinsically-safe handheld field maintenance tool.

* * * * *